US006818181B2

(12) United States Patent
Lee

(10) Patent No.: US 6,818,181 B2
(45) Date of Patent: Nov. 16, 2004

(54) KIT AND METHOD FOR DETECTING FOOD ALLERGIES

(75) Inventor: Martin Jerome Lee, Jersalem (IL)

(73) Assignee: Savyon Diagnostics Ltd., Ashdod (IL)

( * ) Notice: Subject to any disclaimer, the term of this patent is extended or adjusted under 35 U.S.C. 154(b) by 439 days.

(21) Appl. No.: 09/808,039

(22) Filed: Mar. 15, 2001

(65) Prior Publication Data

US 2002/0131893 A1 Sep. 19, 2002

(51) Int. Cl.$^7$ .............................................. G01N 31/00
(52) U.S. Cl. ............................ 422/61; 422/58; 422/50; 422/55; 422/56; 422/68; 422/99; 436/164; 436/169; 436/177; 436/178
(58) Field of Search ........................... 422/61, 68.1, 69, 422/100, 58, 50, 55, 56, 99; 436/518, 164, 169, 177, 178

(56) References Cited

U.S. PATENT DOCUMENTS

| | | | | |
|---|---|---|---|---|
| 4,200,690 A | * | 4/1980 | Root et al. | 435/7.22 |
| 4,842,826 A | * | 6/1989 | Guala | 422/102 |
| 5,198,365 A | * | 3/1993 | Grow et al. | 436/66 |
| 5,389,338 A | | 2/1995 | Fish | |
| 5,480,613 A | * | 1/1996 | Riordan | 422/61 |
| 5,602,040 A | * | 2/1997 | May et al. | 436/514 |
| 6,057,166 A | * | 5/2000 | Childs et al. | 436/525 |
| 6,375,896 B1 | * | 4/2002 | Wuske et al. | 422/58 |
| 6,406,922 B2 | * | 6/2002 | Casterlin et al. | 436/518 |
| 6,667,160 B2 | | 12/2003 | Fine | |

FOREIGN PATENT DOCUMENTS

| | | |
|---|---|---|
| DE | 199 09 891 C1 | 1/2001 |
| WO | WO 94/29696 | 12/1994 |
| WO | WO 97/27484 | 7/1997 |
| WO | WO 98/52044 | 11/1998 |

OTHER PUBLICATIONS

Kolmannskog et al., "Immunoglobin E in Feces from Children with Allergy", Int. Arch Allergy appl. Immun., 76: 133–137 (1985).
Svein Kolmannskog et al., "Immunoglobulin E in Feces from Children with Allergy: Evidence of Local Production of IgE in the Gut", Int. Archs Allergy Appl. Immun., 1985, p. 133–137, vol. 76.
K. Sasai et al., "IgE Levels in Faecal Extracts of Patient with Food Allergy", Allergy, 1992, p. 594–598, vol. 47, Munksgaard.
T. W. Self, "Gastrointestinal Protein Allergy", JAMA, 1969, p. 2393–2396, vol. 207.
David Wild (editor), The Immunoassay Handbook, Second Edition, 2001, p. 159–160, 162, 171, 175–176, 247, 271–277, Nature Publishing Group, London.
M. A. Kerr et al. (editors), Immunochemistry: LabFax, 1994, p. 142–143, BIOS Scientific Publishers Limited, Oxford.
A. Host et al., "Prospective Estimation of IgG, IgG Subclass and IgE Antibodies to Dietary Proteins in Infants with Cow Milk Allergy: Levels of Antibodies to Whole Milk Protein, BLG and Ovalbumin in Relation to Repeated Milk Challenge and Clinical Course of Cow Milk Allergy", Allergy, 1992, p. 218–229, vol. 47.
R. A. Thompson et al., "Hospital Practice: How Necessary are Specific IgE Antibody Tests in Allergy Diagnosis?", The Lancet, Jan. 22, 1983.

* cited by examiner

Primary Examiner—Jill Warden
Assistant Examiner—Sam P. Siefke
(74) Attorney, Agent, or Firm—Browdy and Neimark, P.L.L.C.

(57) ABSTRACT

The invention concerns a home kit and a method for detection of food allergies by determining the presence of antibodies against specific antigens in a stool sample.

15 Claims, 2 Drawing Sheets

KIT AND METHOD FOR DETECTING FOOD ALLERGIES

FIELD OF THE INVENTION

The present invention is generally in the field of kits, and more specifically concerns kits for domestic use for the self-detection of various physiological conditions.

BACKGROUND OF THE INVENTION

The "food allergy" refers to adverse immunologic reactions to food. Food allergy is typically mediated by IgE antibodies directed to a specific food protein, but other immunologic mechanisms can also play a role in this phenomena. The primary target organs for food allergy reactions are the skin, the gastrointestinal tract, and the respiratory system.

Both acute reactions (hives and anaphylaxis) and chronic diseases (asthma, atopic dermatitis and gastrointestinal disorders) may be cause or exacerbated by food allergy.

Foods commonly causing these reactions in children are: milk, eggs, peanuts, soy, wheat, tree-nuts, fish and shellfish. In adults, the most common foods are: peanuts, tree-nuts, shellfish and fruit.

Several specific tests have been developed for the evaluation of IgE-mediated food allergies, in order to identify or exclude responsible foods.

One method of determining the presence of specific IgE antibodies to various allergens, among them food allergens is the "prick-puncture skin testing". While the patient is not taking antihistamines, a device such as bifurcated needle or a lancet is used to puncture the skin through glycinerated extract of a food and also through appropriate positive (histamine) and negative (saline-glycerine) control substances. A local "wheat-and-flare" response indicates the presence of food-specific IgE antibodies, wherein a wheal having a diameter of more than 3 mm is typically considered as indicating a positive response.

Prick skin tests are most valuable when they are negative since the negative predicted value of this test is relatively high (estimated to be above 95% for IgE mediated reactions). However, the positive predicted value of these tests for such IgE mediated reactions is only on an order of 50%. Thus a positive skin test in isolation cannot be considered as a proof of clinically relevant hypersensitivity. Another disadvantage of the prick skin test is that many patients are reluctant to be repeatedly pricked for identifying the responsible food. Furthermore, the test is quite time consuming, typically requiring several test sessions at the practitioner's office, each one for testing several suspected foods.

In vitro blood testing for specific IgE (Radioallergosorbent tests (RAST)) is another option for diagnosing food allergies. As with skin tests a negative result in RAST testing is relatively reliable in ruling out an IgE-mediated reaction to a particular food, however a positive result has low positive predicted value. Another disadvantage of RAST is that it is an invasive test requiring obtaining a blood specimen from the patient and sending it to a laboratory to be analyzed, which analysis is quite expensive. Furthermore, since the test cannot be carried out in the practitioner's office the results are very often delayed.

Double-blind placebo-controlled food challengers are another option for diagnosis of food allergies. According to this option, patients avoid the suspected food for at least two weeks, while discontinuing antihistamine therapy. Other allergy medication, such as anti-asthma medication are reduced as much as possible. Then graded doses of either challenge food or placebo food are administered to the patient. The food is hidden under another food or is taken as capsules as it is consumed without the patient knowing its nature. Medical supervision and immediate access to emergency medications including antihistamines, steroids and inhaled beta antagonists, and equipment for cardiopulmonary resuscitation are required since the allergic reactions can be severe and may even include shock. It is clear that, while such labor intensive and potentially dangerous procedures can detect acute reaction to the food allergies, they can not detect chronic reaction and in no way can be considered as standard procedure for determining allergies to foods.

There have been a number of studies indicating the problematic high false negative results of various food allergies when blood and skin tests are performed (Thompson et al., *The Lancet*, Jan. 22, (1983)).

Further research involved testing the presence of antibodies in mucosal secretions (such as feces) in connection with food allergy testing. It was found that a higher percentage of children with allergy feature IgE in feces compared to the rare occurrence of IgE immunoglobulin in extracts of feces from healthy children (Kolmannskog, *Int. Archs Allergy Applic. Immunol.* 76:133–137, (1985)). The hypothesis was that the IgE may at least in part have been produced locally in the gut mucosa. These findings were supported by the findings that increase Copro IgE (in faecal extracts) are a specific consequence of the local immune response to food allergy simulation in gut mucosa (Sasai et at in *Allergy*, 47:594–598 (1992)).

Self et al. (JAMA, March 31, 707:13, 2393 (1969)) demonstrated stool precipitants against dietary antigens being in children suspected of having various food allergies. These studies indicate the initiation of antibodies to specific food antigens, which could be detected in the stool of the allergic children.

The studies by Self et al. further suggested that the precipitated antibodies are contained in the immunoglobulin A (IgA) fraction of the intestinal secretion, which finding is also in accordance with the fact that most plasma cells of the intestines contain IgA and, unlike serum, intestinal secretions contain large amounts of IgA and lesser amounts of the of other immunoglobulin.

The traditional model of clinical laboratory tests has been that a physician orders a test, a biological specimen such as blood, urine, throat culture, etc. is obtained and sent to a clinical laboratory, and days or weeks later the laboratory result is sent to the physician. The patient then returns to the physician's office to learn result and received advice concerning his or her medical condition. While this model is appropriate for many complicated physiological conditions, there are many other physiological situations where the patient is, or can easily be, well equipped to understand the results of a lab test, has an interest or need to know the result immediately, and is capable of performing the test by himself, and understanding the test results.

Thus, over the past decades home tests for pregnancy have become very popular. Home tests for glucose for diabetic patients have also become very popular. Other tests, such as tests for cholesterol levels, are beginning to gain wide popularity. Still other tests, such as those for day of ovulation are not yet widely known, but are gaining market acceptance.

Thus, a substantial market exists for home diagnostic tests and there is constant need to develop additional home tests for further physiological conditions.

SUMMARY OF THE INVENTION

The present invention is based on the realization that there is a need for a non-invasive, fast, accurate, and user friendly method for diagnosing food allergies, both in adults and in children. The present invention is further based on the realization that detection of food allergy is of the type of detections which may be carried out at home, or at a doctor's clinic, without involving an analyzing laboratory, since the patient (or doctor) can easily understand positive result of a food allergy test, and in many cases can even self treat himself/herself, simply by avoiding the food which caused the food allergy.

The present invention is further based on the realization it is possible to develop a kit for such a non-invasive, reliable and home (and practitioner's office) testing.

The present invention is further based on the realization that such a home kit for determining food allergies, can be constructed for detecting antibodies against food antigens present in stool. Utilization of stool instead of skin or blood as the specimen of the diagnosis of antibodies has the advance that the test is non-invasive, and furthermore features the advantage of greater reliability of antibody testing, as most of the allergic reaction to food takes place in the mucosa of the gastrointestinal tract.

Thus the present invention by its first aspect concerns a home kit for detection of a food allergy in an individual, the kit comprising:

(a) a vessel for mixing a stool specimen with a diluting liquid to produce a diluted stool specimen;

(b) a housing holding within a substrate, the substrate comprising at least one zone containing food antigens, the housing further comprising reagents for producing a visually detected reaction when an antibody-food antigen complex is formed, the housing further comprising at least one conveying means for receiving diluted stool specimen and transferring kit to the food-antigen containing zone of the substrate;

(c) the housing further comprises an indicator for showing the presence of the visually detected reaction.

The term "home kit" in the contents of the present invention refers to the fact that the kit of the invention, and the detection reaction produced therein, does not necessitate any complicated machinery for collecting the specimen and preparing it, for positioning the specimen in the kit, and for reading and interpreting the results—and typically, the results can be viewed by the naked eye, or by simple optical reactor. The term does not necessarily mean that the kit is only operable at home, since due to its non-invasiveness and it is easy, user friendly manner of operation, it can be also used in a practitioner's office or even in hospitals without involving an analytical laboratory.

The kit of the present invention comprises a vessel in which a small amount of stool specimen can be placed and diluted by a suitable diluting liquid. The vessel can then be sealed and the stool and diluting liquid shaken to produce a diluted stool specimen. The diluting liquid may be plain tap water but according to a preferred embodiment of the invention the diluting liquid is, saline, distilled water, 10% formalin solution, sodium acetate solution with or without detergent and the like, and this diluting liquid is also provided as part of the kit's present invention, either a priori present inside the vessel or in a separate container.

The vessel may be for example in the form of a regular capped tube, having graduations, which indicate the volume of the raw stool specimen which is to be placed inside the tube, as well as the amount of the diluting liquid to be added.

The kit may also comprise a construction for collecting the stool, such as a disposable sheet to be placed inside a toilet bowl, a disposable vessel for stool collection, etc., as well as a scooping device, for example in the shape of a small spoon to pick a determined amount of stool. The scooping device (scoop) may be an integral part of the vessel's cap.

The kit's main component is a housing which holds within a substrate, for example, the housing may be a plastic container, having a substrate layer sandwiched between two plastic layers of the container. On a predefined zone of the substrate the food antigens are present, and by a preferred embodiment they are immobilized on the zone. Examples of the substrates are absorbent materials such as nitrocellulose sheets, gel-films, cellulose acetate, fiberglass sheet, paper, agarose gels, and in general any media featuring capillary force or absorbent forces of fluid. Typically the housing has at least one conveying means which can receive the diluted stool specimen and transfer it to said zone. The conveying of the liquid may be by capillary or absorbing flow, which are due to the inherent properties of substrate or inherent properties of a specially designed layer or by the construction of specific flow channels which bring the fluid to the antigen-containing zone.

By one option the conveying means are a combination of openings in the container associated with a construction which can transfer to diluted stool specimen to the zone on the substrate which holds the food antigens and where the antibody-antigen interaction takes place. For example, the conveying means are in the shape of an opening in the housing through which a small amount of the diluted stool can be poured. The stool is then transferred to the antigen-containing zone of the substrate, for example, by capillary forces either of the substrate itself (which is made of absorbent material) or by capillary or absorbed forces of a specially designed layer which sole purpose is to transfer the diluted stool to the antigen containing zone, or by flow in specially designed channels.

By another option the conveying means is an absorbent material or material composed of capillaries which protrudes out of the housing, for example, an absorbent stick protruding out of an opening in the housing. In such a case the protruding substrate material is dipped in the diluted stool and due to capillary forces the liquid is transferred to the antigen-containing zone which is present inside the housing.

The antigens may be immobilized on the substrate by an interaction such as covalent bonds, hydrogen bonds, electrostatic forces contained within voids of beads, etc.

Typically, large particles have to be filtered out of the diluted stool before the diluted stool is conveyed to the antigen-containing zone of the substrate. Said filtering may take place in the vessel itself, for example by constructing a two part cap: the more distal part serving as a seal, which hermetically closes the vessel and allows the user to vigorously mix its contents. However, this cap may be opened fully or partially to expose below a filter sieve which can ensure that only relatively small particles are poured from the vessel into the convening means.

Alternatively, the housing itself may comprise said filtering sieve, which for example may be present either at the mouth of the opening of the convening means, or may be present as a continuous filter sieve layer above the substrate zone on which the food antigens are present.

By a preferred option where the substrate is an absorbent material, the stool particles may be sieved on its upper layers of the substrate so that a filtered specimen reaches the layer of immobilized antigen.

The food antigens should be chosen in connection with the type of food allergy which is to be detected by the kit of the invention.

By one embodiment, the kit may comprise a single food antigen and in such a case it can give a binary (yes/no) indication, whether the individual is allergic to that specific antigen. Alternatively, the indication may be semi-quantitative, for example, by giving three shades of the same color—a darker shade indicating "high" (level of antibody and allergy), than medium shade "medium", and light shade "low".

By another embodiment, the kit of the present invention includes a plurality of food antigens, and in such a case it is possible to determine, in a single assay, whether the individual is allergic to a variety of foods.

Kits in accordance with a preferred embodiment are generally divided into two groups: kits for children and kits for adults and these are chosen with the most common foods which cause allergy in any of these two groups.

The kits for children typically include the most common in food antigens to which children are allergic and include the following:

(a) antigens from cow's milk (which may include BLG, ovalbumin, casein) or whole extracts of milk;

(b) antigens from soy protein (which may include whole extracts of soy);

(c) antigens for peanuts which include whole extracts of peanuts;

(d) antigens from wheat which include whole extracts, or gluten from milk;

(e) antigens to eggs which include whole extracts of egg.

Kits for adults typically include antigens from various vegetables and fruits, grains and nuts.

Antigens for the above are commercially available from a plurality of sources and may include protein as well as non-protein. Typically, regions of the substrate surrounding the zone on which the antigen is immobilized are saturated by non-specific hydrophilic polymers such as bovine serum albumin, other proteins, or polyethylene glycol to block unspecific binding of the antibody to the substrate.

Interaction between the food antigens, a priori present in the kit, and antibodies which are present in the stool specimen, yields an antigen-antibody complex. In the kit of the invention the presence of such a complex should produce a visually detected reaction—i.e. a reaction which produces a visible indication, which may be viewed either by the naked eye, or by an optical reader. Examples of such a reaction is a color reaction (achieved by ELISA method) or a precipitation reaction which can easily be detected. A plurality of methods for producing visually detected reaction for antigen-antibody complexes are well known in the art, for example, as specified in "*Immunoassay Handbook*" by David Wild $2^{nd}$ Edition, Nature Publishing Gropu, pp. 150–175 and 271–277. An example is indirect ELISA, a procedure which is used to identify the presence of antibodies utilizing, for example, anti-human antibodies conjugated to a visually detectable moiety (such as gold particles) or conjugated to an enzyme producing a color reactor). Another possibility is by detection of the presence of antibody-antigen aggregates, for example, as specified in the publication of Self (Supra).

The indicator is typically an opening in the housing ("a window"), which allows direct viewing of the visually detected reaction. Typically the opening is immediately above the region on which the antigens are immobilized. The view may be by the naked eye, for example, by the detection of colored bar, or a colored dot, or alternatively may be viewed by an optical reader, to increase sensitivity.

Where a single food antigen is to be detected, a single indicator can be used which when showing the indicator (color bar, dot, etc.) indicates that there exists antibodies to the specific food antigen.

Where a plurality of food allergies are to be detected a plurality of indicators (windows) can be used so that each indicator is associated with a single food allergy. Alternatively, a single indicator giving different readings can be used wherein each reading is in accordance with the specific antigen-antibody complex formed and thus each reading is indicative of a different food antigen.

For example, where five different food allergies are to be tested, it is possible to construct a housing with five different and separate antigen containing substrate zones, so that in each zone a different food antigen will be immobilized, and for each zone there will be associated a separate indicator. This will ensure that the visually detected reaction in each zone is specific to the food antigen present on the substrate of said zone, and the indicator ("window") will simply be specifically associated with each zone. In the above case the housing may have a single means convening for example in the form of an absorbent layer.

The liquid stool specimen is poured into an opening, and due to the fact that the substrate is absorbent, capillary forces present in the absorbent material, cause transfer of the diluted stool specimen through all the separate zones on which are immobilized different food antigens. Then, the specific visually detected reaction is formed in each separate zone which reaction can be viewed by the specific indicator associated with that zone (for example by a "window" the container through which a colored bead can be viewed).

In accordance with a preferred embodiment of the invention the kit also contains internal control. The internal control is composed of antibodies against the antigens of the kit present, a priori, in the zone of the antigens. The purpose of these, a priori, present food antibodies, is to form aggregates with the food antigens, to produce a visually detected reaction, in order to determine that the reagents used for producing the reaction are functioning properly.

The antibodies detected by the kit of the invention may be any antibody, monoclonal or polyclonal against a food antigen but typically the kit detects total immunoglobulins, or alternatively, IgA, and also IgE antibodies.

The present invention also concerns a method for detecting the presence of a food allergy in an individual, suspected of having such an allergy, the method comprising:

(a) obtaining a stool specimen from the individual;

(b) diluting the stool specimen with a diluting liquid to produce a diluted stool specimen;

(c) introducing the stool specimen into the kit of the invention; and (d) viewing the indicator, the presence of a visually detected reaction in the indicator, indicating the presence of food allergy in the individual.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
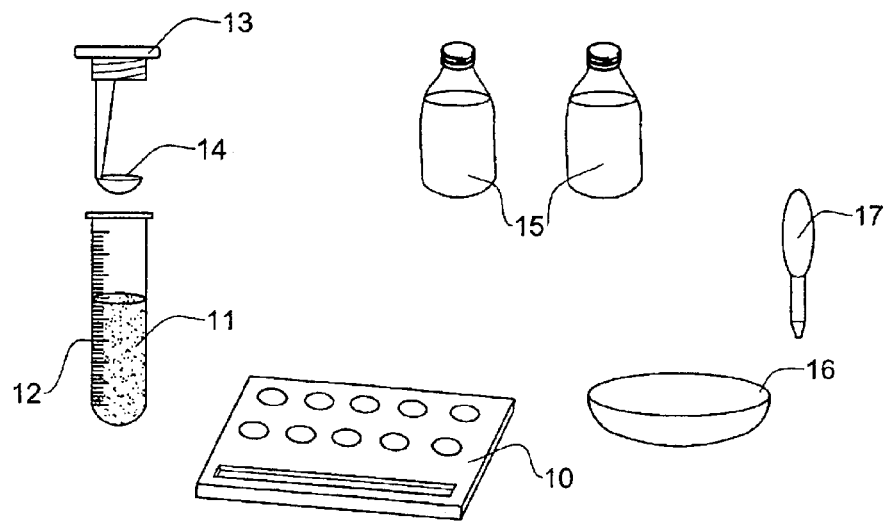
FIG. 1 shows a schematic representation of the components of the kit of the invention.

Reference is made to FIG. 1 which shows basically an example of the various components of the kit of the invention.

The main component of the kit of the invention is a housing 10 holding within a substrate on which are immobilized various food antigens, as will be explained in more detail in FIGS. 2 and 3 and on which the detection actually takes place. In addition, the kit comprises a vessel 11 into which stool specimen is placed. Typically the volume in the vessel contains 5–10 cc of liquid as may contain graduations 12 to measure the amount of liquid. Cap 13 of the vessel is engagable with vessel 11, and once closed can form a hermetically closed seal so that the vessel can be vigorously shaken to dilute the stool specimen with the diluting liquid.

By the embodiment shown in FIG. 1, the cap 13 has as an integral part also scooping spoon 14 which can pick up a small amount of stool, and once the cap is fully engaged with the tube 11, the spoon is immersed inside the liquid in the tube and thus cause dilution of the stool. The kit also comprises liquid bottles 15 which may contain, for example, the diluting liquid, and in some cases, reagents required to produce a color reaction (to be specified in more detail hereinafter). Finally, the kit also contains a device 16, in the form of a small disposable container, for collecting the stool.

Where it is desired to add reagents present in bottle 15, the kit may also contain a small pipette 17.

Figure 2A:
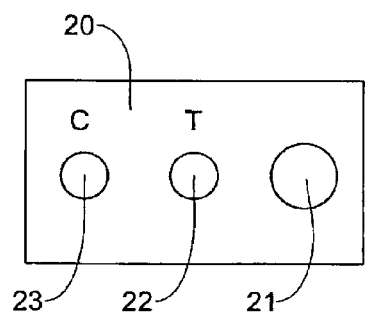
FIG. 2A shows one embodiment of the housing of the invention having the substrate fully contained within the housing, for detecting a single food allergy.

Reference is now made to FIG. 2A which shows the housing of the kit of the present invention 20. Typically, the housing is made out of plastic material, and holds within an absorbent material such as nitrocellulose. In the housing, three openings are evident, 21, 22 and 23. Into opening 21, a minute amount of diluted stool sample is added.[it probalby will require a specific number of drops] Then, due to the capillary forces of the nitrocellulose substrate present within housing 20, the liquid advances towards opening 22 and 23. Opening 22 (T) is the test indicator and present above the region of the substrate on which the antigens are immobilized. The antigens are specific food antigens for which the allergy is to be determined. If the stool sample contains antibodies against the specific antigen present on the substrate in region 22, an antibody-antigen aggregate is formed, which can be viewed, for example, as a dark dot in opening 22.

Opening 23 is a control zone C in opening 22, and that zone, specific antigen is also immobilized. Antibody to that specific antigen may be present in a zone directly adjacent to the antibody, and carried to it by the sample fluid. Alternativley, antibody to the specific antigen may be present a priori, as aggregates of the antigen bound to the antibody to that specific antigen. The purpose of opening 23 is to test the quality of the system in forming the visually detected reaction. By another option the antibody and antigen may be separated and form the aggregate only in situ in the housing of the invention.

Once the aggregate of antibody-antigens are formed in test region T (and a priori present in control region C), they can be detected by any manner known in the art. In a manner, they are detected by the use of anti-human an antibodies which are conjugated to a detectable moiety. The detectable moiety for example may be a gold particle which may be visualized directly, or alternatively may be an enzyme such as alkaline phosphatase, which can produce a color reaction if provided with its appropriate substrate such as para-nitro phenyl phosphate (see for example in the publication of "the Immunoassay Handbook supra") Other detectable labels such as fluorescent labels and peroxidase enzymes are also available.

The anti-human antibody conjugated to the detectable label may be added, after a phase of time (allowing the antibody in the antibody-containing region to react with the antigen in the sample) to occur, simply by adding, from an external tube, the appropriate anti-human antibody, optionally together with the substrate for the reaction.

By another option, the anti-human antibody (either with the gold particle or with the enzyme) may be present at a different layer than layer on which the food antigen is present, for example, present in a layer below that of the food antigen. Between two layers there is present a dissolvable layer, which is slowly degraded by fluids in the specimen. This ensures that there is time for degradation of the layer, allowing first the antibody in the test sample to react with the antigen and only later the anti-human antibodies are reacted.

Figure 2B:
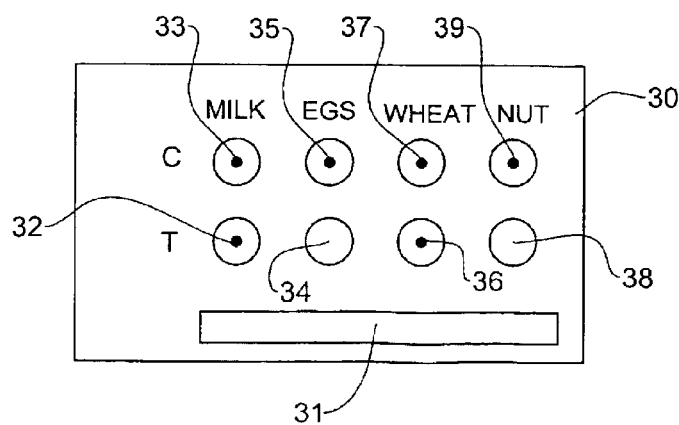
FIG. 2B shows another embodiment of the housing of the type shown in FIG. 2A for detecting a plurality of food allergies.

FIG. 2B shows essentially the same construct as FIG. 2A, out for the detection of a plurality of food allergies, in the present case for the detection of four different food allergies. The housing 30 has an elongated opening 31 on which the sample is poured. Then, by capillary forces the fluid advances towards the other end of the housing. Openings 32, 34, 36 and 38 show test results, i.e. are above the zone of the substrate containing immobilized antigens. Openings 33, 35, 37 and 39 are control openings, i.e. in above the zones of the substrates on which are immobilized both the antigens and a priori present antibodies. The reaction take essentially as explained in 2A above. In the present case, all the control openings have a dot indicator, indicating that the reagents function properly. In the test samples, there is an indicator in openings 32 and 36, indicating that the tested individual is allergic both to milk and to wheat.

Figure 3A:
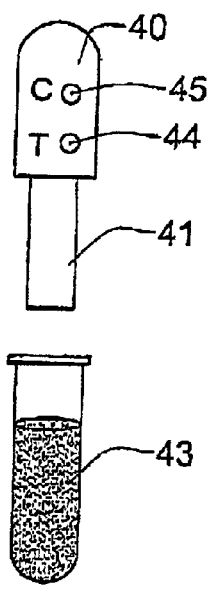
FIG. 3A shows an embodiment of a housing containing a substrate protruding out of the housing for detecting a single food allergy.

Reference is made to FIG. 3A which shows another embodiment for the housing of the invention. Housing 40 contains within substrate, such as a nitrocellulose sheet, which protrudes, in the form of a stick 41 out of the end of the housing, Then, the protruding end of the substrate may be dipped inside the vessel 43 containing the diluted stool sample. As explained above, by capillary forces, the sample advances, and through openings 44 and 45, it can be determined whether a color reaction takes place both in the test (T) and the control (C) indicators (opening).

Figure 3B:
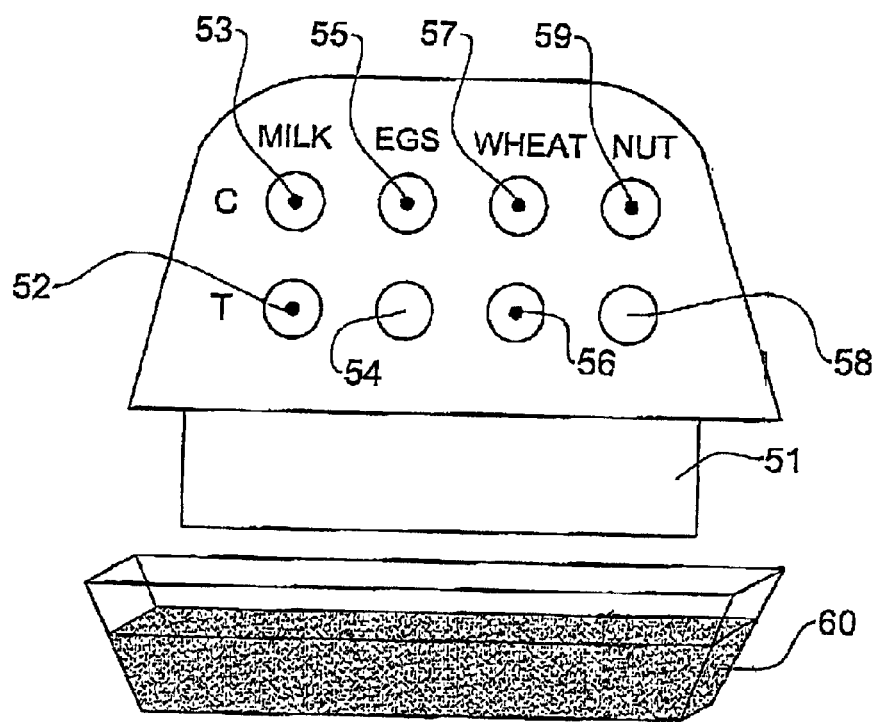
FIG. 3B shows a housing containing a substrate protruding out of the housing for detecting a plurality of food allergies.

FIG. 3B shows a similar apparatus to that in 3A 50, having a protruding substrate therefrom 51. However, in this case instead of having one indicator in the form of an opening test and one indicator for control, there a four indicators for the test (T) 52, 54, 56 and 58 and four indicators for the control (C) 53, 55, 57 and 59. After the sample has been diluted, it is poured to an elongated open vessel 60, and the protruding substrate 51 is dipped in this liquid containing vessel. Then, the liquid advances to the zones of the antigen of the test, or the antigen-antibody of the control, and a color reaction may be determined. In the present case, as can be seen, the controls are appropriate, and the person is allergic to milk and to wheat as indicated by the presence of colored dots.

What is claimed is:

1. A home and/or doctor's office test kit for detection of a food allergy in an individual, the kit comprising:
   (a) a vessel for mixing a stool specimen with a diluting liquid to produce a diluted stool specimen;
   (b) a housing separate from said vessel and holding therewithin a substrate,
   the substrate comprising at least one zone containing food antigens,
   the housing further comprising reagents for producing a visually detected reaction when an antibody-food antigen complex is formed,
   the housing further comprising at least one conveying means for receiving diluting stool specimen and transferring it to the food-antigen containing zone of the substrate;
   (c) wherein the housing further comprises an indicator for showing the presence of the visually detected reaction for the presence of antibodies against food antigens.

2. A kit according to claim 1, wherein the food antigens are immobilized on the substrate in the zone containing the food antigens.

3. A kit according to claim 1, wherein the substrate has a capillary structure and the conveying means are the capillary forces of the substrate.

4. A kit according to claim 1, wherein the substrate has a porous structure and the conveying means are the absorbent forces of the substrate.

5. A kit according to claim 1, wherein the substrate is selected from: nitrocellulose sheets, paper, gel-films, cellulose acetate, glass fibers, glass papers, and agarose gel.

6. A kit according to claim 1, wherein the indicator is an opening in a housing showing above the zone of the substrate containing the food antigens.

7. A kit according to claim 1, wherein the diluting liquid is selected from distilled water, formalin solution, sodium acetate solution, sodium acetate solution with a detergent.

8. A kit according to claim 1, wherein the visually detected reaction is obtained by binding of an anti-human antibody, conjugated to a detectable label, to antibody-food antigen complex.

9. A kit according to claim 8, wherein the anti-human antibody is conjugated to a gold particle.

10. A kit according to claim 8, wherein the anti-human antibody is conjugated to an enzyme capable in the presence of a suitable substrate, to produce a visually detected reaction.

11. A kit according to claim 1, for the detection of a single food allergy.

12. A kit according to claim 1, for the. detection of two or more food allergies, wherein each antigen for the detection of the food allergy, is immobilized on a separate zone on the substrate, and wherein each indicator is an opening in the housing above said separate zone.

13. A kit according to claim 1, further comprising a scooping device.

14. A kit according to claim 13, wherein the scooping device is an integral part of a cap for the vessel.

15. A kit according to claim 1, further comprising a disposable container for collecting stools.

* * * * *